US008368401B2

(12) United States Patent
Levy et al.

(10) Patent No.: US 8,368,401 B2
(45) Date of Patent: Feb. 5, 2013

(54) TECHNIQUES FOR CORRECTING MEASUREMENT ARTIFACTS IN MAGNETIC RESONANCE THERMOMETRY

(75) Inventors: Yoav Levy, Hinanit (IL); Arik Hananel, Tel Aviv-Jaffa (IL); David Freundlich, Haifa (IL); Gilad Halevy, Modi'in (IL); Benny Assif, Ramat HaSharon (IL); Hadas Ziso, Kiryat Tivon (IL)

(73) Assignee: Insightec Ltd., Tirat Carmel (IL)

( * ) Notice: Subject to any disclaimer, the term of this patent is extended or adjusted under 35 U.S.C. 154(b) by 599 days.

(21) Appl. No.: 12/615,780

(22) Filed: Nov. 10, 2009

(65) Prior Publication Data

US 2011/0109309 A1 May 12, 2011

(51) Int. Cl.
G01V 3/00 (2006.01)

(52) U.S. Cl. ......... 324/315; 324/317; 600/410

(58) Field of Classification Search ............ 324/315, 324/317; 600/410, 412, 413, 420
See application file for complete search history.

(56) References Cited

U.S. PATENT DOCUMENTS

| | | |
|---|---|---|
| 2,795,709 A | 6/1957 | Camp |
| 3,142,035 A | 7/1964 | Harris |
| 3,942,150 A | 3/1976 | Booth et al. |
| 3,974,475 A | 8/1976 | Burckhardt et al. |
| 3,992,693 A | 11/1976 | Martin et al. |
| 4,000,493 A | 12/1976 | Spaulding et al. |
| 4,339,952 A | 7/1982 | Foster |
| 4,454,597 A | 6/1984 | Sullivan |
| 4,478,083 A | 10/1984 | Hassler et al. |
| 4,505,156 A | 3/1985 | Questo |
| 4,526,168 A | 7/1985 | Hassler et al. |
| 4,537,074 A | 8/1985 | Dietz |
| 4,549,533 A | 10/1985 | Cain et al. |
| 4,554,925 A | 11/1985 | Young |
| 4,558,279 A | 12/1985 | Ackerman et al. |
| 4,858,597 A | 8/1989 | Kurtze et al. |
| 4,865,042 A | 9/1989 | Umemura et al. |
| 4,888,746 A | 12/1989 | Wurster et al. |
| 4,889,122 A | 12/1989 | Watmough et al. |
| 4,893,284 A | 1/1990 | Magrane |

(Continued)

FOREIGN PATENT DOCUMENTS

| | | |
|---|---|---|
| DE | 4345308 C2 | 2/2001 |
| EP | 0560397 | 9/1993 |

(Continued)

OTHER PUBLICATIONS

Rieke et al., "Referenceless MR Thermometry for Monitoring Thermal Ablation in the Prostate," IEEE Transactions on Medical Imaging, pp. 813-821 (Jun. 1, 2007).

(Continued)

Primary Examiner — Louis Arana
(74) Attorney, Agent, or Firm — Bingham McCutchen LLP

(57) ABSTRACT

Techniques for correcting measurement artifacts in MR thermometry predict or anticipate movements of objects in or near an MR imaging region that may potentially affect a phase background and then acquire a library of reference phase images corresponding to different phase backgrounds that result from the predicted movements. For each phase image subsequently acquired, one reference phase image is selected from the library of reference phase images to serve as the baseline image for temperature measurement purposes. To avoid measurement artifacts that arise from phase wrapping, the phase shift associated with each phase image is calculated incrementally, that is, by accumulating phase increments from each pair of consecutively scanned phase images.

16 Claims, 5 Drawing Sheets

U.S. PATENT DOCUMENTS

| | | |
|---|---|---|
| 4,937,767 A | 6/1990 | Reuschel et al. |
| 5,209,221 A | 5/1993 | Riedlinger |
| 5,247,935 A | 9/1993 | Cline et al. |
| 5,271,400 A | 12/1993 | Dumoulin et al. |
| 5,275,165 A | 1/1994 | Ettinger et al. |
| 5,284,144 A | 2/1994 | Delannoy et al. |
| 5,291,890 A | 3/1994 | Cline et al. |
| 5,307,812 A | 5/1994 | Hardy et al. |
| 5,307,816 A | 5/1994 | Hashimoto et al. |
| 5,318,025 A | 6/1994 | Dumoulin et al. |
| 5,323,779 A | 6/1994 | Hardy et al. |
| 5,327,884 A | 7/1994 | Hardy et al. |
| 5,329,930 A | 7/1994 | Thomas, III et al. |
| 5,368,031 A | 11/1994 | Cline et al. |
| 5,368,032 A | 11/1994 | Cline et al. |
| 5,378,987 A | 1/1995 | Ishihara et al. |
| 5,379,642 A | 1/1995 | Reckwerdt et al. |
| 5,391,140 A | 2/1995 | Schaetzle et al. |
| 5,413,550 A | 5/1995 | Castel |
| 5,443,068 A | 8/1995 | Cline et al. |
| 5,474,071 A | 12/1995 | Chapelon et al. |
| 5,485,839 A | 1/1996 | Aida et al. |
| 5,490,840 A | 2/1996 | Uzgiris et al. |
| 5,507,790 A | 4/1996 | Weiss |
| 5,520,188 A | 5/1996 | Hennige et al. |
| 5,526,814 A | 6/1996 | Cline et al. |
| 5,549,638 A | 8/1996 | Burdette |
| 5,553,618 A | 9/1996 | Suzuki et al. |
| 5,573,497 A | 11/1996 | Chapelon |
| 5,582,578 A | 12/1996 | Zhong et al. |
| 5,590,653 A | 1/1997 | Aida et al. |
| 5,590,657 A | 1/1997 | Cain et al. |
| 5,601,526 A | 2/1997 | Chapelon et al. |
| 5,605,154 A | 2/1997 | Ries et al. |
| 5,617,371 A | 4/1997 | Williams |
| 5,617,857 A | 4/1997 | Chader et al. |
| 5,643,179 A | 7/1997 | Fujimoto |
| 5,662,170 A | 9/1997 | Donovan et al. |
| 5,665,054 A | 9/1997 | Dory |
| 5,666,954 A | 9/1997 | Chapelon et al. |
| 5,676,673 A | 10/1997 | Ferre et al. |
| 5,687,729 A | 11/1997 | Schaetzle |
| 5,694,936 A | 12/1997 | Fujimoto et al. |
| 5,711,300 A | 1/1998 | Schneider et al. |
| 5,722,411 A | 3/1998 | Suzuki et al. |
| 5,739,625 A | 4/1998 | Falcus |
| 5,743,863 A | 4/1998 | Chapelon |
| 5,752,515 A | 5/1998 | Jolesz et al. |
| 5,759,162 A | 6/1998 | Oppelt et al. |
| 5,769,790 A | 6/1998 | Watkins et al. |
| 5,810,008 A | 9/1998 | Dekel et al. |
| 5,873,845 A | 2/1999 | Cline et al. |
| 5,897,495 A | 4/1999 | Aida et al. |
| 5,916,161 A | 6/1999 | Ishihara et al. |
| 5,938,600 A | 8/1999 | Van Vaals et al. |
| 5,938,608 A | 8/1999 | Bieger et al. |
| 5,947,900 A | 9/1999 | Derbyshire et al. |
| 5,984,881 A | 11/1999 | Ishibashi et al. |
| 6,004,269 A | 12/1999 | Crowley et al. |
| 6,023,636 A | 2/2000 | Wendt et al. |
| 6,042,556 A | 3/2000 | Beach et al. |
| 6,064,206 A | 5/2000 | Van Vaals et al. |
| 6,067,371 A | 5/2000 | Gouge et al. |
| 6,071,239 A | 6/2000 | Cribbs et al. |
| 6,113,559 A | 9/2000 | Klopotek |
| 6,128,522 A | 10/2000 | Acker et al. |
| 6,128,958 A | 10/2000 | Cain |
| 6,193,659 B1 | 2/2001 | Ramamurthy et al. |
| 6,194,899 B1 | 2/2001 | Ishihara et al. |
| 6,242,915 B1 | 6/2001 | Hurd |
| 6,263,230 B1 | 7/2001 | Haynor et al. |
| 6,267,734 B1 | 7/2001 | Ishibashi et al. |
| 6,289,233 B1 | 9/2001 | Dumoulin et al. |
| 6,309,355 B1 | 10/2001 | Cain et al. |
| 6,334,846 B1 | 1/2002 | Ishibashi et al. |
| 6,374,132 B1 | 4/2002 | Acker et al. |
| 6,377,834 B1 | 4/2002 | Zhou et al. |
| 6,392,330 B1 | 5/2002 | Zloter et al. |
| 6,397,094 B1 | 5/2002 | Ludeke et al. |
| 6,413,216 B1 | 7/2002 | Cain et al. |
| 6,419,648 B1 | 7/2002 | Vitek et al. |
| 6,424,597 B1 | 7/2002 | Bolomey et al. |
| 6,425,867 B1 | 7/2002 | Vaezy et al. |
| 6,428,532 B1 | 8/2002 | Doukas et al. |
| 6,461,314 B1 | 10/2002 | Pant et al. |
| 6,475,150 B2 | 11/2002 | Haddad |
| 6,478,739 B1 | 11/2002 | Hong |
| 6,506,154 B1 | 1/2003 | Ezion et al. |
| 6,506,171 B1 | 1/2003 | Vitek et al. |
| 6,511,428 B1 | 1/2003 | Azuma et al. |
| 6,522,142 B1 | 2/2003 | Freundlich et al. |
| 6,523,272 B1 | 2/2003 | Morales |
| 6,542,767 B1 | 4/2003 | McNichols et al. |
| 6,559,644 B2 | 5/2003 | Froundlich et al. |
| 6,566,878 B1 | 5/2003 | Komura et al. |
| 6,582,381 B1 | 6/2003 | Yehezkeli et al. |
| 6,599,256 B1 | 7/2003 | Acker et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1 | 9/2003 | Freundlich et al. |
| 6,626,854 B2 | 9/2003 | Friedman et al. |
| 6,626,855 B1 | 9/2003 | Weng et al. |
| 6,629,929 B1 | 10/2003 | Jago et al. |
| 6,645,162 B2 | 11/2003 | Friedman et al. |
| 6,666,833 B1 | 12/2003 | Friedman et al. |
| 6,676,601 B1 | 1/2004 | Lacoste et al. |
| 6,679,855 B2 | 1/2004 | Horn et al. |
| 6,705,994 B2 | 3/2004 | Vortman et al. |
| 6,719,694 B2 | 4/2004 | Weng et al. |
| 6,733,450 B1 | 5/2004 | Alexandrov et al. |
| 6,735,461 B2 | 5/2004 | Vitek et al. |
| 6,761,691 B2 | 7/2004 | Tsuzuki |
| 6,770,031 B2 | 8/2004 | Hynynen et al. |
| 6,770,039 B2 | 8/2004 | Zhong et al. |
| 6,788,619 B2 | 9/2004 | Calvert |
| 6,790,180 B2 | 9/2004 | Vitek |
| 6,824,516 B2 | 11/2004 | Batten et al. |
| 6,951,540 B2 | 10/2005 | Ebbini et al. |
| 6,961,606 B2 | 11/2005 | DeSilets et al. |
| 7,001,379 B2 | 2/2006 | Behl et al. |
| 7,062,415 B2 | 6/2006 | Whitefield et al. |
| 7,077,820 B1 | 7/2006 | Kadziauskas et al. |
| 7,094,205 B2 | 8/2006 | Marmarelis |
| 7,128,711 B2 | 10/2006 | Medan et al. |
| 7,175,596 B2 | 2/2007 | Vitek et al. |
| 7,175,599 B2 | 2/2007 | Hynynen et al. |
| 7,264,592 B2 | 9/2007 | Shehada |
| 7,264,597 B2 | 9/2007 | Cathignol |
| 7,267,650 B2 | 9/2007 | Chow et al. |
| 7,344,509 B2 | 3/2008 | Hynynen et al. |
| 7,359,745 B2 * | 4/2008 | Lewin et al. ............... 600/410 |
| 7,377,900 B2 | 5/2008 | Vitek et al. |
| 7,505,808 B2 | 3/2009 | Anderson et al. |
| 7,510,536 B2 | 3/2009 | Foley et al. |
| 7,511,501 B2 | 3/2009 | Wexler |
| 7,535,794 B2 | 5/2009 | Prus et al. |
| 7,553,284 B2 | 6/2009 | Vaitekunas |
| 7,603,162 B2 | 10/2009 | Danz et al. |
| 7,611,462 B2 | 11/2009 | Vortman et al. |
| 7,652,410 B2 | 1/2010 | Prus |
| 7,699,780 B2 | 4/2010 | Vitek et al. |
| 2001/0031922 A1 | 10/2001 | Weng et al. |
| 2002/0035779 A1 | 3/2002 | Krieg et al. |
| 2002/0082589 A1 | 6/2002 | Friedman et al. |
| 2003/0004439 A1 | 1/2003 | Pant et al. |
| 2003/0060820 A1 | 3/2003 | Maguire et al. |
| 2003/0187371 A1 | 10/2003 | Vortman et al. |
| 2004/0030251 A1 | 2/2004 | Ebbini et al. |
| 2004/0068186 A1 | 4/2004 | Ishida et al. |
| 2004/0122323 A1 | 6/2004 | Vortman et al. |
| 2004/0210134 A1 | 10/2004 | Hynynen et al. |
| 2005/0033201 A1 | 2/2005 | Takahashi et al. |
| 2005/0096542 A1 | 5/2005 | Weng et al. |
| 2005/0203444 A1 | 9/2005 | Schonenberger et al. |
| 2005/0251046 A1 | 11/2005 | Yamamoto et al. |

| | | | |
|---|---|---|---|
| 2006/0052661 | A1 | 3/2006 | Gannot et al. |
| 2006/0052701 | A1 | 3/2006 | Carter et al. |
| 2006/0058678 | A1 | 3/2006 | Vitek et al. |
| 2006/0106300 | A1 | 5/2006 | Seppenwoolde et al. |
| 2007/0055140 | A1 | 3/2007 | Kuroda |
| 2007/0239062 | A1 | 10/2007 | Chopra et al. |
| 2009/0096450 | A1 | 4/2009 | Roland |
| 2011/0046472 | A1 | 2/2011 | Schmidt et al. |
| 2011/0046475 | A1 | 2/2011 | Assif et al. |

FOREIGN PATENT DOCUMENTS

| | | |
|---|---|---|
| EP | 1582886 | 10/2005 |
| EP | 1774920 A1 | 4/2007 |
| FR | 2806611 A1 | 9/2001 |
| JP | 11313833 A | 11/1999 |
| WO | WO-9100059 A1 | 1/1991 |
| WO | WO-9852465 A1 | 11/1998 |
| WO | WO-00316144 A1 | 6/2000 |
| WO | WO-0166189 A1 | 9/2001 |
| WO | WO-0180709 A2 | 11/2001 |
| WO | WO-0258791 A1 | 8/2002 |
| WO | WO-03/013654 A1 | 2/2003 |
| WO | WO-03097162 A2 | 11/2003 |
| WO | WO-03098232 A2 | 11/2003 |
| WO | WO-200558029 A2 | 6/2005 |
| WO | WO-2006018837 A2 | 2/2006 |
| WO | WO-2006025001 A1 | 3/2006 |
| WO | WO-2006087649 A1 | 8/2006 |
| WO | WO-2007073551 A1 | 6/2007 |
| WO | WO-2008050278 A1 | 5/2008 |
| WO | WO-200875203 A2 | 6/2008 |
| WO | WO-2008/119054 | 10/2008 |
| WO | WO-2009/055587 | 4/2009 |

OTHER PUBLICATIONS

Suprijanto et al., "Inter-frame Motion Correction for MR Thermometry," Medical Image Computing and Computer-Assisted Intervention—MIC CAI 2005 Lecture Notes in Computer Science, pp. 580-588 (Jan. 2005).
De Senneville et al., "Motion Correction in MR Thermometry of Abdominal Organs: A Comparison of the Referenceless vs. the Multibaseline Approach," Magnetic Resonance in Medicine, vol. 64, pp. 1373-1381 (Jul. 2010).
Li et al., "An Internal Reference Model-Based PRF Temperature Mapping Method with Cramer-Rao Lower Bound Noise Performance Analysis," Magnetic Resonance in Medicine, vol. 62, pp. 1251-1260 (Sep. 2009).
Wissler, "Pennes' 1948 Paper Revisited," Journal of Applied Physiology, vol. 85, pp. 35-41 (1998).
Romero-Méndez et al., "Analytical Solution of the Pennes Equation for Burn-Depth Determination From Infrared Thermographs," Mathematical Medicine and Biology, vol. 27, pp. 21-38 (Jul. 2009).
Dragonu et al., "Perfusion Calculation Based on MR-Temperature Maps and Focused Ultrasound Heating. Theoretical and Experimental Study," Intl. Society for Magnetic Resonance in Medicine, vol. 16, p. 1223 (May 3, 2008).
Chopra et al., "Method for MRI-Guided Conformal Thermal Therapy of Prostate with Planar Transurethral Ultrasound Heating Applicators; Method for Conformal Prostate Thermal Therapy," Physics in Medicine and Biology, vol. 50, No. 21, pp. 4957-4975 (Nov. 7, 2005).
Salomir et al., "Hyperthermia by MR-Guided Focused Ultrasound: Accurate Temperature Control Based on Fast MRI and a Physical Model of Local Energy Deposition and Heat Conduction," Magnetic Resonance in Medicine, vol. 43, No. 3, pp. 342-347 (Mar. 1, 2000).
International Search Report and Written Opinion mailed Mar. 31, 2011 for International Application No. PCT/IB2010/003038 (20 pages).
Bouchard et al., "Magnetic Resonance Imaging of Thermal Coagulation Effects in a Phantom for Calibrating Thermal Therapy Devices," Medical Physics, vol. 27, No. 5, pp. 1141-1145 (May 1, 2000).
Wlodarczyk et al, "Corrections and Calibration of MR Thermography for Hyperthermia Monitoring in the Hyperthermia/ MR Hybrid System," Proceedings of the Intl. Soc. for Magnetic Resonance in Medicine, 12th Scientific Meeting and Exhibition, p. 977 (May 1, 2004).
Wang et al., "Sensitivity Study of MR-Based Temperature Mapping at 7T," Proceedings of the Intl. Society for Magnetic Resonance in Medicine, Joint Annual Meeting ISMRM-ESMRMB, p. 3377 (May 5, 2007).
McDannold et al., " Usefulness of MR Imaging-Derived Thermometry and Dosimetry in Determining the Threshold for Tissue Damage Induced by Thermal Surgery in Rabbits," Radiology, vol. 216 pp. 517-523 (2000).
Suprijanto et al., "Displacement Correction Scheme for MR-Guided Interstitial Laser Therapy," Ellis RE, Peters TM (Eds.): "MiCCAI 2003, LNCS 2879," pp. 399-407 (2003).
Shmatukha et al., "Correction of Proton Resonance Frequency Shift Proton Resonance Frequency Shift Temperature Maps for Magnetic Field Disturbances Caused by Breathing; Correction of Proton Resonance Frequency Shift Temperature Maps," Physics in Medicine and Biology, vol. 51, No. 18 pp. 4689-4705 (Sep. 21, 2006).
De Senneville et al., "An Optimised Multi-Baseline Approach for On-Line MR-Temperature Monitoring on Commodity Graphics Hardware," Biomedical Imaging, pp. 1513-1516 (May 14, 2008).
Botros et al., "A hybrid computational model for ultrasound phased-array heating in presence of strongly scattering obstacles," IEEE Trans. On Biomed. Eng., vol. 44, No. 11, pp. 1039-1050 (Nov. 1997).
Cain et al., "Concentric-ring and Sector-vortex Phased-array Applicators for Ultrasound Hperthermia," IEEE Trans. On Microwave Theory & Techniques, vol. MTT-34, No. 5, pp. 542-551 (May 1986).
Chen et al., "MR Acoustic Radiation Force Imaging: Comparison of Encoding Gradients."
Cline et al., "Focused US system for MR imaging-guide tumor ablation," Radiology, v. 194, No. 3, pp. 731-738 (Mar. 1995).
Cline et al., "MR Temperature mapping of focused ultrasound surgery," Magnetic Resonance in Medicine, vol. 32, No. 6, pp. 628-636 (1994).
Cline et al., "Simultaneous magnetic resonance phase and magnitude temperature maps in muscle," Magnetic Resonance in Medicine, vol. 35, No. 3, pp. 309-315 (Mar. 1996).
Daum et al., "Design and evaluation of a feedback based phased array system for ultrasound surgery," IEEE Trans. Ultrason. Ferroelec. Freq. Control, vol. 45, No. 2, pp. 431-434 (1998).
de Senneville et al., "Real-time adaptive methods for treatment of mobile organs by MRI-controlled high-intensity focussed Ultrasound," Magnetic Resonance in Medicine 57:319-330 (2007).
Fjield et al, "The Combined Concentric-ring and Sector-vortex Phased Array for MRI Guided Ultrasound Surgery," IEEE Trans. On Ultrasonics, Ferroelectrics and Freq. Cont., vol. 44, No. 5, pp. 1157-1167 (Sep. 1997).
Herbert et al., "Energy-based adaptive focusing of waves: application to ultrasonic transcranial therapy," 8th Intl. Symp. On Therapeutic Ultrasound.
Huber et al., "A New Noninvasive Approach in Breast Cancer Therapy Using Magnetic Resonance Imaging-Guided Focussed Ultrasound Surgery," Cancer Research 61, 8441-8447 (Dec. 2001).
International Preliminary Report on Patentability in International Patent Application No. PCT/IB2004/001512, mailed Dec. 8, 2005.
International Search Report and Written Opinion in International Patent Application No. PCT/IB2004/001498, dated Aug. 31, 2004.
International Search Report and Written Opinion in International Patent Application No. PCT/IB2005/002273, mailed Dec. 20, 2005.
International Search Report and Written Opinion in International Patent Application No. PCT/IB2005/002413, mailed Nov. 22, 2005.
International Search Report and Written Opinion in International Patent Application No. PCT/IB2006/001641, mailed Sep. 25, 2006.
International Search Report and Written Opinion in International Patent Application No. PCT/IB2006/003300, mailed Feb. 14, 2008.
International Search Report and Written Opinion in International Patent Application No. PCT/IB2007/001079, mailed Dec. 10, 2007.
International Search Report and Written Opinion in International Patent Application No. PCT/IB2007/002134, mailed Dec. 13, 2007.
International Search Report and Written Opinion in International Patent Application No. PCT/IB2007/002140, mailed Dec. 29, 2008.

International Search Report and Written Opinion in International Patent Application No. PCT/IB2008/003069, mailed Apr. 27, 2009.
Jolesz et al., "Integration of interventional MRI with computer-assisted surgery," J. Magnetic Resonance Imaging. 12:69-77 (2001).
Maxwell et al., "Noninvasive thrombolysis using pulsed ultrasound cavitation therapy—Histotripsy," Abstract, U.S. Natl. Lib. of Med., NIH, Ultrasound Med. Biol. (Oct. 23, 2009).
McDannold et al., "MRI evaluation of thermal ablation of tumors and focused ultrasounds," JMRI vol. 8, No. 1, pp. 91-100 (1998).
McDannold et al., "Magnetic resonance acoustic radiation force imaging," Med. Phys. vol. 35, No. 8, pp. 3748-3758 (Aug. 2008).
Medel et al., "Sonothrombolysis: An emerging modality for the management of stroke," Neurosurgery, vol. 65, No. 5, pp. 979-993.
Partial International Search Report and Written Opinion in International Patent Application No. PCT/IB2007/001079, dated Sep. 25, 2007.
Vimeux et al., "Real-time control of focused ultrasound heating based on rapid MR thermometry," Investig. Radiology, vol. 43, No. 3, pp. 190-193.
Vykhodtseva et al., "MRI detection of the thermal effects of focused ultrasound on the brain," Ultrasound in Med. & Biol., vol. 26, No. 5, pp. 871-880 (2000).
Written Opinion in International Patent Application No. PCT/IL01/00340, mailed Feb. 24, 2003.
Written Opinion in International Patent Application No. PCT/IL02/00477, mailed Feb. 25, 2003.
Written Opinion in International Patent Application No. PCT/IB03/05551, mailed Sep. 10, 2004.
"How is Ablatherm treatment performed?" http://www.edap-hifu.com/eng/physicians/hifu/3c_treatment_treat-description.htm, accessed Jan. 3, 2003.
"What is HIFU? HIFU: High Intensity Focused Ultrasound," http://www.edap-hifu.com/eng/physicians/hifu2a_hifu_overview.htm, accessed Jan. 3, 2003.
"What are the physical principles?" http://www.edap-hifu.com/eng/physicians/hifu/2c_hifu_physical.htm, accessed Jan. 3, 2003.
"How does HIFU create a lesion?" http://www.edap-hifu.com/eng/physicians/hifu/2d_hifu_lesion.htm, accessed Jan. 3, 2003.
"Prostate Cancer Phase I Clinical Trials Using High Intensity Focused Ultrasound (HIFU)," Focus Surgery, http://www.focus-surgery.com/PCT%20Treatment%20with%20HIFU.htm, accessed Jan. 3, 2003.
"Abstract" Focus Surgery, http://www.focus-surgery.com/Sanghvi.htm, accessed Jan. 3, 2003.
Exablate 2000 Specification, InSightec, Ltd. (2 pages).
FDA Approves Exablate 2000 as Non-invasive surgery for Fibroids, Oct. 22, 2004.
International Search Report and Written Opinion in International Patent Application No. PCT/IB2010/000189, mailed Jun. 1, 2010.
International Search Report for PCT/IB03/05551 completion date Mar. 2, 2004 (5 pages).
International Search Report and Written Opinion in Internation Patent Application No. PCT/IB2010/000971, mailed Jul. 29, 2010 (9 pages).
Charles Mougenot, et al, "MR Monitoring of the Near-Field HIFU Heating," 8th International Symposium on Therapeutic Ultrasound, edited by E. S. Ebbini, University of Minnesota, Sep. 10-13, 2009.
Max O. Kohler, et al, "Volumetric HFU Ablation guided by Multiplane MRI Thermometry," 8th International Symposium on Therapeutic Ultrasound, edited by E. S. Ebbini, University of Minnesota, Sep. 10-13, 2009.
Kowalski et al, "Optimization of electromagnetic phased-arrays for hyperthermia via magnetic resonance temperature estimation," Biomedical Engineering, IEEE Transactions on vol. 49, Issue 11, Nov. 2002, pp. 1229-1241.

Beerlage et al., "Current Status of Minimally Invasive Treatment Options for Localized Prostate Carcinoma," European Urology, vol. 47, No. 1 pp. 2-13 (Jan. 2000).
Boyd et al., "Convex Optimization," Cambridge University Press, UK (2004).
Chartrand et al., "Iteratively Reweighted Algorithms for Compressive Sensing," IEEE ICASSP, pp. 3869-3872 (Apr. 2008).
Funai et al., "Regularized Field Map Estimation in MRI," IEEE Trans.Med. Imaging, vol. 27, No. 10, pp. 1484-1494 (Oct. 2008).
Grissom et al., "Hybrid Referenceless and Multibaseline Subtraction MR Thermometry for Monitoring Thermal Therapies in Moving Organs," Medical Physics, vol. 37, No. 9. pp. 5014-5026 (Sep. 2010).
Grissom et al. "Reference-less MR Thermometry Using Iteratively-Reweighted $\zeta 1$ Regression," Proc. Intl. Soc. Mag. Reson. Med., vol. 17, p. 444 (2009).
Grissom et al., "Regularized Multicoil MR Thermometry," Proc. Intl. Soc. Mag. Reson. Med., vol. 17, p. 2516 (2009).
Grissom et al., "Regularized Referenceless Temperature Estimation in PRF-Shift MR Thermometry," IEEE, pp. 1235-1238 (2009).
Holbrook et al., "Real-Time MR Thermometry for Monitoring HIFU Ablations of the Liver," Magnetic Resonance in Medicine, vol. 63, pp. 365-373 (2010).
Ishihara et al., "A Precise and Fast Temperature Mapping Using Water Proton Chemicl Shift," MRM, vol. 34, pp. 814-823 (1995).
Kokuryo et al., "Method for Target Tracking in Focused Ultrasound Surgery of Liver Using Magnetic Resonance Filtered Venography," IEEE EMBS, pp. 2614-2617 (2007).
Kuroda et al., "Optimization of Self-Reference Thermometry Using Complex Field Estimation," Magnetic Resonance in Medicine, vol. 56, pp. 835-843 (2006).
Larson et al., "Histological Changes of Minimally Invasive Procedures for the Treatment of Benign Prostatic Hyperplasia and Prostate Cancer: Clinical Implications," The Journal of Urology, vol. 170, pp. 12-19 (Jul. 2003).
Mougenot et al., "MR monitoring of the near-field HIFU heating," 8th Intl. Symp. On Therapeutic Ultrasound, edited by E.S. Ebbini, U. of Minn. (Sep. 2009).
Nayak et al., "Real-Time Cardiac MRI at 3 Tesla," Magnetic Resonance in Medicine, vol. 51, pp. 655-660 (2004).
Rieke et al., "Referenceless PRF Shift Thermometry," Magnetic Resonance in Medicine, vol. 51, pp. 1223-1231 (2004).
Roujol et al., "Advanced in Real-Time MR Temperature Mapping of the Human Heart," Proc. Intl. Soc. Mag. Reson. Med. vol. 17, p. 443 (2009).
Shinohara "Thermal Ablation of Prostate Diseases: Advantages and Limitations," Int. Journal of Hyperthermia, vol. 20, No. 7, pp. 679-697 (Nov. 2004).
Soher et al., "Correcting for BO Field Drift in MR Temperature Mapping with Oil References," Proceedings of the Intl. Society for Magnetic Resonance in Medicine (May 2008).
Vigen et al., "Triggered, Navigated, Multi-Baseline Method for Proton Resonance Frequency Temperature Mapping with Respiratory Motion," Magnetic Resonance in Medicine, vol. 50, pp. 1003-1010 (2003).
De Senneville et al., "Real-Time Adaptive methods for Treatment of Mobile Organs by MRI-Controlled High-Intensity Focused Ultrasound," Magnetic Resonance in Medicine, vol. 57, pp. 319-330 (2007).
DeZwart et al., "On-Line Correction and Visualization of Motion During MRI-Controlled Hyperthermia," Magnetic Resonance in Medicine, vol. 45, No. 1, pp. 128-137 (Jan. 1, 2001).

* cited by examiner

TECHNIQUES FOR CORRECTING MEASUREMENT ARTIFACTS IN MAGNETIC RESONANCE THERMOMETRY

FIELD OF THE INVENTION

The present invention relates generally to magnetic resonance (MR) imaging, and more particularly, to techniques for correcting measurement artifacts in MR thermometry.

BACKGROUND OF THE INVENTION

MR imaging of internal body tissues may be used for numerous medical procedures, including diagnosis and surgery. In general terms, MR imaging starts by placing a subject in a relatively uniform, static magnetic field. The static magnetic field causes hydrogen nuclei spins to align and precess about the general direction of the magnetic field. Radio frequency (RF) magnetic field pulses are then superimposed on the static magnetic field to cause some of the aligned spins to alternate between a temporary high-energy non-aligned state and the aligned state, thereby inducing an RF response signal, called the MR echo or MR response signal. It is known that different tissues in the subject produce different MR response signals, and this property can be used to create contrast in an MR image. One or more RF receivers detect the duration and strength of the MR response signals, and such data are then processed to generate tomographic or three-dimensional images.

MR imaging can also be used effectively during a medical procedure to assist in locating and guiding medical instruments. For example, a medical procedure can be performed on a patient using medical instruments while the patient is in an MRI machine. The medical instruments may be for insertion into a patient or they may be used externally but still have a therapeutic or diagnostic effect. For instance, the medical instrument can be an ultrasonic device, which is disposed outside a patient's body and focuses ultrasonic energy to ablate or necrose tissue or other material on or within the patient's body. The MRI machine preferably produces images at a high rate so that the location of the instrument (or the focus of its effects) relative to the patient may be monitored in real-time (or substantially in real-time). The MRI machine can be used for both imaging the targeted body tissue and locating the instrument, such that the tissue image and the overlaid instrument image can help track an absolute location of the instrument as well as its location relative to the patient's body tissue.

MR imaging can further provide a non-invasive means of quantitatively monitoring in vivo temperatures. This is particularly useful in the above-mentioned MR-guided focused ultrasound (MRgFUS) treatment or other MR-guided thermal therapy where temperature of a treatment area should be continuously monitored in order to assess the progress of treatment and correct for local differences in heat conduction and energy absorption. The monitoring (e.g., measurement and/or mapping) of temperature with MR imaging is generally referred to as MR thermometry or MR thermal imaging.

Among the various methods available for MR thermometry, the proton-resonance frequency (PRF) shift method is often preferred due to its excellent linearity with respect to temperature change, near-independence from tissue type, and high sensitivity. The PRF shift method is based on the phenomenon that the MR resonance frequency of protons in water molecules changes linearly with temperature. Since the frequency change is small, only −0.01 ppm/° C. for bulk water and approximately −0.0096 to −0.013 ppm/° C. in tissue, the phase shift is typically detected with a phase-sensitive imaging method in which the imaging is performed twice: first to acquire a baseline phase image prior to a temperature change and then to acquire a second image after the temperature change, thereby capturing a small phase change that is proportional to the change in temperature.

A phase image, for example, may be computed from an MR image, and a temperature-difference map relative to the baseline image may be obtained by (i) determining, on a pixel-by-pixel basis, phase differences between the phase image corresponding to the baseline and the phase image corresponding to a subsequently obtained MR image, and (ii) converting the phase differences into temperature differences based on the PRF temperature dependence while taking into account imaging parameters such as the strength of the static magnetic field and echo time (TE). It should be appreciated that, although a subtraction step may be involved, the determination of the phase differences involves more than a simple subtraction of scalars.

Unfortunately, changes in phase images do not arise uniquely from temperature changes. Various non-temperature-related factors, such as changes in a local magnetic field due to nearby moving objects, magnetic susceptibility changes in a patient's body due to breathing or other movements, and magnet or shim drifts can all lead to confounding phase shifts that may render a phase-sensitive temperature measurement invalid. For example, during some MR-guided thermal treatment procedures, one or more treatment devices need to be re-positioned and/or re-oriented in or near the MR imaging area. Since the treatment devices typically include metal components, their movements could perturb local magnetic fields and thereby significantly change the phase background. Non-metal objects and their movements may also perturb local magnetic fields. The patient's breathing or turning motions, for example, could have similar effects. In fact, the changes in magnetic field associated with patient motion and/or nearby objects can be severe enough to render temperature measurements made using the above-mentioned phase-sensitive approach useless.

Further measurement artifacts may arise from "phase wrapping" when significant temperature changes are monitored over a long time period, such as during a lengthy treatment procedure. In existing PRF-based temperature measurements, each phase image is compared directly with an initial baseline reference to determine the amount of phase shift. However, if the accumulated phase shift has exceeded $\pi$ in any part of a recently acquired phase image—a condition referred to as "phase wrapping"—the true magnitude of phase shift will not be captured by simply subtracting the baseline reference image from the recently acquired phase image.

In view of the foregoing, it may be understood that there are significant problems and shortcomings associated with current PRF techniques.

SUMMARY

Embodiments of the present invention provide for the correction of measurement artifacts in MR thermometry. In particular, during a reference-acquisition phase, phase images are obtained to correspond with positions and/or orientations of a treatment device—e.g., an ultrasonic transducer—that will occur during treatment; an MRgFUS treatment session, for example, may involve multiple sonications each performed with the transducer at a different physical location relative to the patient. A library of reference phase images is therefore acquired at different points along the path, at least at locations (and, desirably, reflecting transducer orientations) where sonications are to be performed during treatment. These reference images reflect the different phase backgrounds for various possible treatment-device positionings during treatment. As actual treatment proceeds, transducer movements are predicted, and one reference phase image is selected from the library of reference phase images to serve as the baseline image for temperature-measurement purposes. To avoid measurement artifacts that arise from phase wrapping, the phase shift associated with each phase image is calculated incrementally, that is, by accumulating phase increments from each pair of consecutive phase images.

In one particular exemplary embodiment, a method of performing PRF-based MR temperature measurement may involve acquiring a plurality of reference phase images of an MR imaging region, where each of the reference images corresponds to a phase background resulting from a different arrangement of one or more devices in or near the MR imaging region. The method may also comprise the steps of acquiring a first phase image of the MR imaging region subsequent to the acquisition of the plurality of reference phase images; selecting, from the plurality of reference phase images, a first reference phase image most closely corresponding to the first phase image; and calculating a first phase shift based at least in part on a difference between the first phase image and the first reference phase image. In various embodiments, the further involves acquiring a second phase image of the MR imaging region subsequent to the acquisition of the first phase image; selecting, from the plurality of reference phase images, a second reference phase image most closely corresponding to the second phase image; and calculating a second phase shift by summing (i) the first phase shift and (ii) an incremental phase shift of the second phase image as compared to the first phase image. At least one temperature change may be determined based on at least one of the first phase shift and the second phase shift.

In another particular exemplary embodiment, a system for performing PRF-based MR temperature measurement comprises an MRI unit and a control module in communication with the MRI unit. The control module is configured to cause the MRI unit to (i) acquire a plurality of reference phase images of an MR imaging region, where each of the reference images corresponds to a phase background resulting from a different arrangement of one or more devices in or near the MR imaging region; (ii) acquire a first phase image of the MR imaging region subsequent to the acquisition of the plurality of reference phase images; and (iii) acquire a second phase image of the MR imaging region subsequent to the acquisition of the first phase image. The system may further comprise a processor module having access to image data acquired by the MRI unit. The processor module is configured to (i) select, from the plurality of reference phase images, a first reference phase image most closely corresponding to the first phase image; (ii) calculate a first phase shift based at least in part on a difference between the first phase image and the first reference phase image; (iii) select, from the plurality of reference phase images, a second reference phase image most closely corresponding to the second phase image; (iv) calculate a second phase shift based at least in part on a difference between the second phase image and the second reference phase image; and (v) determine at least one temperature change based on at least one of the first phase shift and the second phase shift.

In yet another particular exemplary embodiment, a computer-readable medium storing computer-executable codes for causing at least one processor to performing PRF-based MR temperature measurement may comprise computer-executable code for causing acquisition of a plurality of reference phase images of an MR imaging region, where each of the reference images corresponds to a phase background resulting from a different arrangement of one or more devices in or near the MR imaging region. The computer-readable medium may also comprise computer-executable code for causing acquisition of a first phase image of the MR imaging region subsequent to the acquisition of the plurality of reference phase images; computer-executable code for causing selection, from the plurality of reference phase images, a first reference phase image most closely corresponding to the first phase image; and computer-executable code for causing calculation of a first phase shift based at least in part on a difference between the first phase image and the first reference phase image. In some embodiments, the computer-readable medium further comprises computer-executable code for causing acquisition of a second phase image of the MR imaging region subsequent to the acquisition of the first phase image; computer-executable code for causing selection, from the plurality of reference phase images, a second reference phase image most closely corresponding to the second phase image; and computer-executable code for causing calculation of a second phase shift by summing (i) the first phase shift and (ii) an incremental phase shift of the second phase image as compared to the first phase image. The computer-readable medium may additionally comprise computer-executable code for causing determination of at least one temperature change based on at least one of the first phase shift and the second phase shift.

In still another particular exemplary embodiment, a method of performing PRF-based MR temperature measurement may comprise the step of acquiring a plurality of reference phase images of an MR imaging region, where each of the reference phase images corresponds to a phase background resulting from one or more predicted anatomical movements of at least a part of a patient's body. The method may also comprise the steps of acquiring a first phase image of the MR imaging region subsequent to the acquisition of the plurality of reference phase images; selecting, from the plurality of reference phase images, a first reference phase image most closely corresponding to the first phase image; and calculating a first phase shift based at least in part on a difference between the first phase image and the first reference phase image. In various embodiments, the method further comprises the steps of acquiring a second phase image of the MR imaging region subsequent to the acquisition of the first phase image; selecting, from the plurality of reference phase images, a second reference phase image most closely corresponding to the second phase image; and calculating a second phase shift by summing (i) the first phase shift and (ii) an incremental phase shift of the second phase image as compared to the first phase image. At least one temperature change may be determined based on at least one of the first phase shift and the second phase shift.

In a further particular exemplary embodiment, a method of performing PRF-based MR temperature measurement may comprise the step of acquiring a plurality of reference phase images of an MR imaging region associated with a patient, where each of the reference images correspond to a phase background resulting from a different arrangement of one or more devices in or near the MR imaging region in combination with one or more predicted movements of the patient. The method may also comprise the step of acquiring a first phase image of the MR imaging region subsequent to the acquisition of the plurality of reference phase images. The method may further comprise the step of selecting, from the plurality of reference phase images, a first reference phase image most closely corresponding to the first phase image. The method may additionally comprise determining at least one temperature change based at least in part on a difference between the first phase image and the first reference phase image.

Embodiments of related systems and computer-readable media implementing the method are also disclosed.

The present invention will now be described in more detail with reference to exemplary embodiments thereof as shown in the accompanying drawings. While the present invention is described below with reference to exemplary embodiments, it should be understood that the present invention is not limited thereto. Those of ordinary skill in the art having access to the teachings herein will recognize additional implementations, modifications, and embodiments, as well as other fields of use, which are within the scope of the present invention as described herein, and with respect to which the present invention may be of significant utility.

BRIEF DESCRIPTION OF THE DRAWINGS

In order to facilitate a fuller understanding of the present invention, reference is now made to the accompanying drawings, in which like elements are referenced with like numerals. These drawings should not be construed as limiting the present invention, but are intended to be exemplary only.

DETAILED DESCRIPTION

Embodiments of the present invention improve the utility and robustness of MR thermometry, as described below, to measure temperatures and compensate for phase shifts that arise from factors other than temperature changes.

Figure 1:
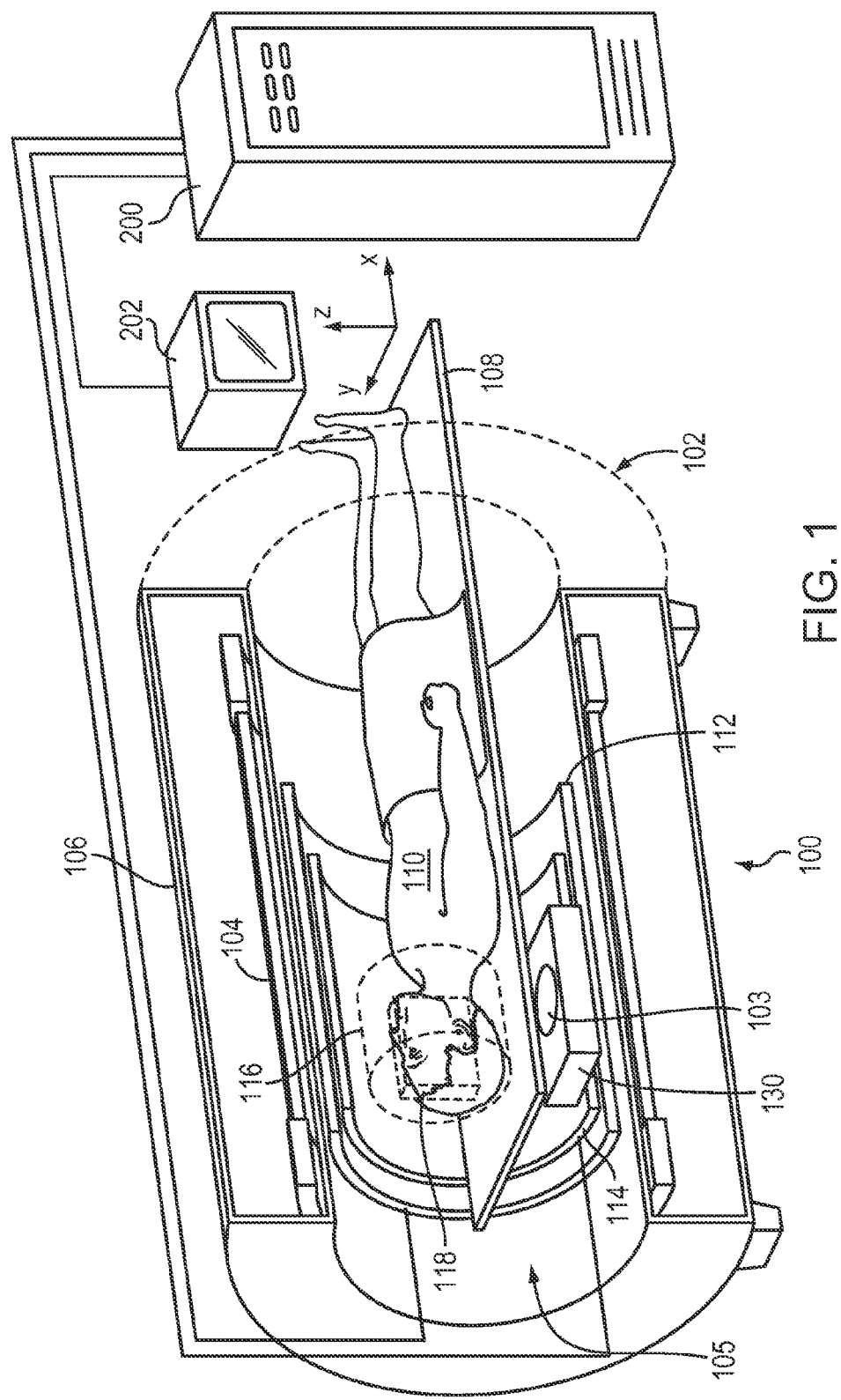
FIG. 1 shows an exemplary MRI system in or for which the techniques for correcting measurement artifacts in MR thermometry in accordance with the present invention may be implemented.

FIG. 1 shows an exemplary MRI system in or for which the techniques for correcting measurement artifacts in MR thermometry in accordance with the present invention may be implemented. The illustrated MRI system 100 comprises an MRI machine 102. If an MR-guided procedure is being performed, a medical device 103 may be disposed within the bore of the MRI machine 102. Since the components and operation of the MRI machine are well-known in the art, only some basic components helpful in the understanding of the system 100 and its operation will be described herein.

The MRI machine 102 typically comprises a cylindrical electromagnet 104, which generates a static magnetic field within a bore 105 of the electromagnet 104. The electromagnet 104 generates a substantially homogeneous magnetic field within an imaging region 116 inside the magnet bore 105. The electromagnet 104 may be enclosed in a magnet housing 106. A support table 108, upon which a patient 110 lies, is disposed within the magnet bore 105. A region of interest 118 within the patient 110 may be identified and positioned within the imaging region 116 of the MRI machine 102.

A set of cylindrical magnetic field gradient coils 112 may also be provided within the magnet bore 105. The gradient coils 112 also surround the patient 110. The gradient coils 112 can generate magnetic field gradients of predetermined magnitudes, at predetermined times, and in three mutually orthogonal directions within the magnet bore 105. With the field gradients, different spatial locations can be associated with different precession frequencies, thereby giving an MR image its spatial resolution. An RF transmitter coil 114 surrounds the imaging region 116 and the region of interest 118. The RF transmitter coil 114 emits RF energy in the form of a magnetic field into the imaging region 116, including into the region of interest 118.

The RF transmitter coil 114 can also receive MR response signals emitted from the region of interest 118. The MR response signals are amplified, conditioned and digitized into raw data using an image-processing system 200, as is known by those of ordinary skill in the art. The image-processing system 200 further processes the raw data using known computational methods, including fast Fourier transform (FFT), into an array of image data. The image data may then be displayed on a monitor 202, such as a computer CRT, LCD display or other suitable display.

The medical device 103 (in a transducer housing 130) may also be placed in or near the imaging region 116 of the MRI machine 102. In the example shown in FIG. 1, the medical device 103 may be an ultrasonic instrument used for ablating tissue such as fibroids or cancerous (or non-cancerous) tissue, for breaking up occlusion within vessels, or for performing other treatment of tissues on or within the patient 110. In fact, the medical device 103 can be any type of medical instrument including, without limitation, a needle, catheter, guidewire, radiation transmitter, endoscope, laparoscope, or other instrument. In addition, the medical device 103 can be configured either for placement outside the patient 110 or for insertion into the patient body.

Figure 2:
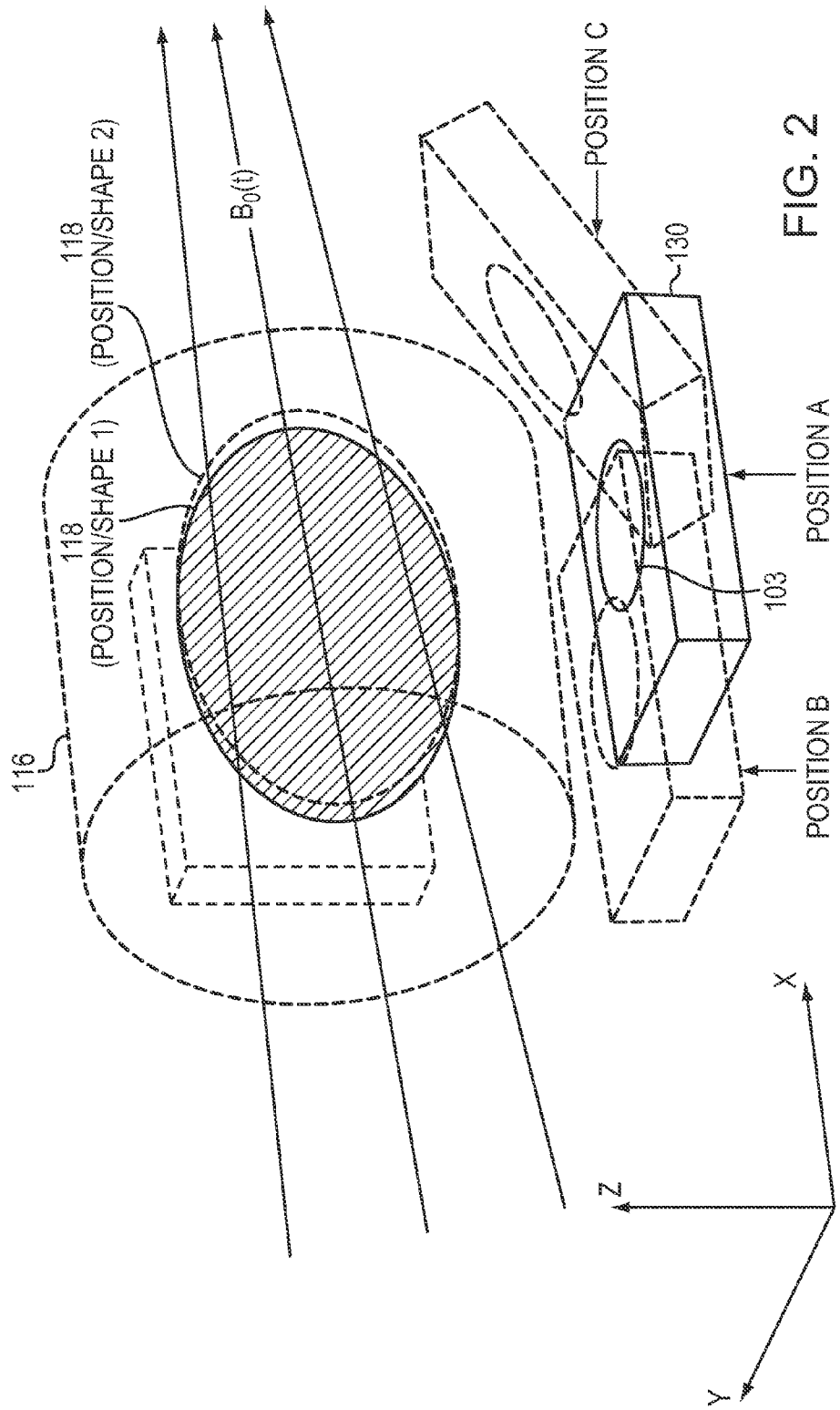
FIG. 2 shows an MR imaging region and illustrates exemplary movements of objects that may be addressed by techniques in accordance with the present invention.

The imaging region 116 (including the region of interest 118) is enlarged in FIG. 2, to illustrate exemplary movements of objects that may be addressed by techniques in accordance with the present invention.

During MR thermal imaging (or any medical procedure involving MR temperature mapping) of the region 116, the region of interest 118, which is typically a part of a patient's body, may change its shape and/or position due to movements of the patient's body. For example, if the region of interest 118 is the patient's head (as shown in FIG. 1), it may turn slightly either to the left or to the right during the thermal imaging process. If the region of interest 118 is part of the patient's abdominal area, its shape may contract or expand with the patient's respiratory cycle. As a result, at a first moment, the region of interest 118 may show up in an MR image with Position/Shape 1, and at a second moment, the region of interest 118 may show up in the MR image with Position/Shape 2. The changes in shape and/or position of the region of interest 118 not only affect its registration in the MR image but can also perturb the magnetic field $B_0(t)$ thereby altering the phase background.

Similarly, during a medical procedure involving MR temperature mapping of the region 116, the medical device 103 (together with its housing 130) may be re-positioned and/or re-oriented one or more times according to a dynamic setup. The medical device 103 may first assume an original position or Position A. Sometime during the treatment procedure, the medical device 103 may be shifted or translated to Position B while maintaining its original orientation. Alternatively or additionally, the medical device 103 may be moved to Position C, which involves both translation and rotation of the medical device 103. Any of these movements can change the magnetic field $B_0(t)$ and therefore the phase background.

Although only one medical device 103 is shown in FIGS. 1 and 2, it should be appreciated that the movements of multiple medical devices and/or other metal object(s) in or near the imaging region 116 may cause similar measurement artifacts. Furthermore, the movements of medical device(s) and other objects may occur in combination with movements of the patient's body.

According to embodiments of the present invention, at least some of the above-described movements of objects in or near the MR imaging region may be predicted or anticipated before a thermal imaging process starts. For example, a dynamic setup of medical device(s) is often planned well before commencement of a medical procedure. Thus, it is known in advance and with sufficient certainty as to where each medical device will be approximately positioned and how it will be approximately oriented relative to the MR imaging region or the treatment area. Similarly, certain natural movements of the patient's body are predictable, such as the regular heaving and ebbing of an abdominal region during a respiratory cycle. Other potential movements of the patient's body could be anticipated, such as slight turning and/or tilting of the head or sliding of the hands or arms. The predictable nature of object movements in or near the MR imaging region can be exploited, by its self or in combination with mathematical techniques, to help reduce measurement artifacts that might arise from such movements, as will be explained in detail below.

Figure 3:
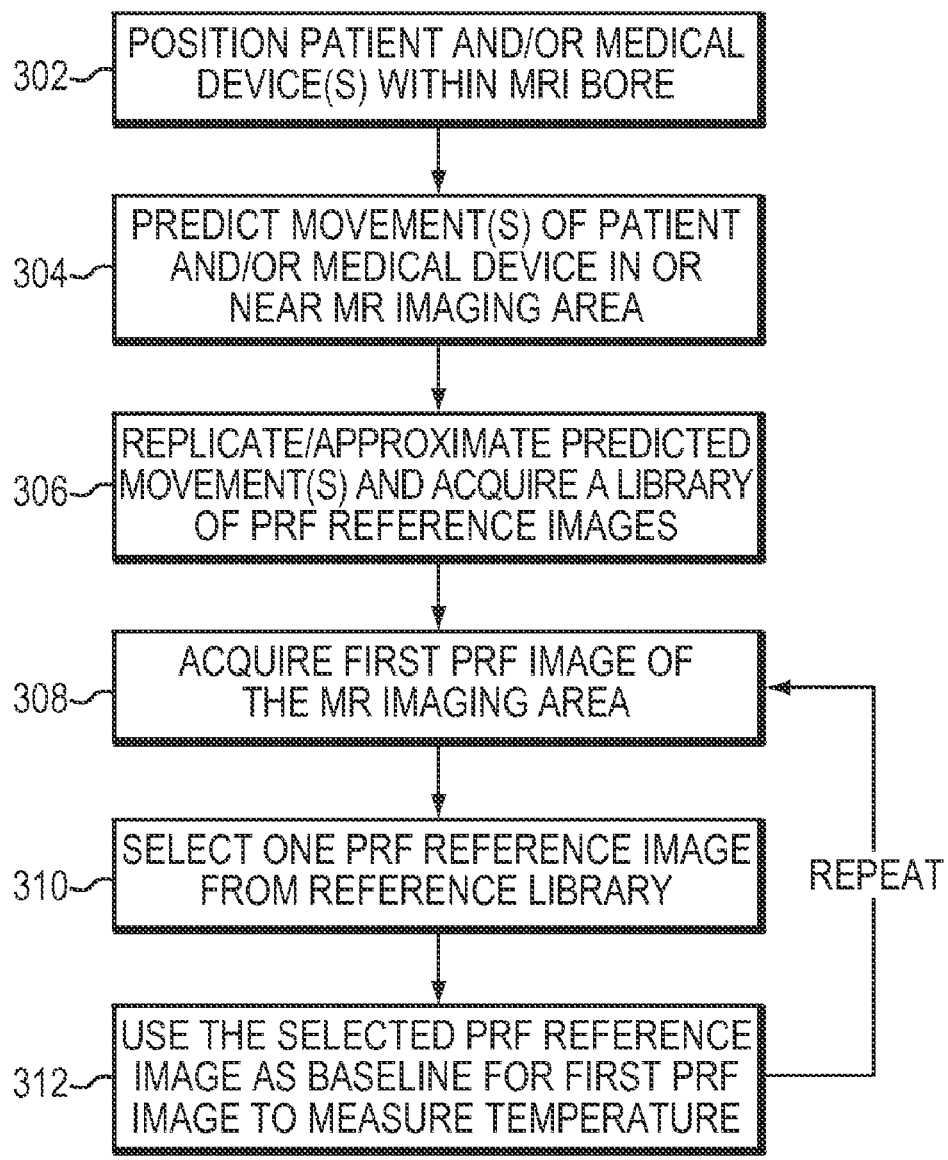
FIG. 3 shows a flow chart illustrating an exemplary method for correcting measurement artifacts in MR thermometry in accordance with an embodiment of the present invention.

FIG. 3 shows a flow chart illustrating an exemplary method for correcting measurement artifacts in MR thermometry in accordance with an embodiment of the present invention. In step 302, a subject such as a human body, is positioned within a bore of an MRI machine. A region of interest (ROI) in the subject may be identified for purposes of MR temperature measurement, that is, MR thermal imaging or temperature mapping. For example, the region of interest may be a portion of a human body, such as the head region (118) as shown in FIG. 1. In an MR-guided medical procedure, the region of interest may be or include a particular portion of a human body upon which the procedure is performed. For instance, in an MRgFUS procedure, the region of interest may include a general tissue area into which ultrasonic energy is to be focused. One or more medical devices, for use in a treatment or therapeutic procedure, may also be positioned in or near the MR imaging area or the region of interest.

In step 304, movements of the patient and/or medical device(s) are predicted. For example, if a dynamic setup of medical device(s) will be implemented in a thermal treatment procedure, it may be determined where and how each medical device will be positioned during each stage of the treatment procedure. If the patient's breathing motion might be significant, a trajectory within a range of movement may be predicted for a relevant part of the patient's body, such as a treatment region. The treatment region may follow and repeat the predicted trajectory in substantial synchronization with the patient's respiratory cycles. If it is anticipated that the patient might move his head, hands, or arms, the extent or range of such movements may also be estimated.

In step 306, the predicted movement(s) can be replicated or approximated, individually and/or in combination, and a library of reference phase images that result from the predicted movement(s) or combination thereof are acquired. In other words, a "dry run" of the treatment procedure is performed in step 306, with the patient in place, to capture possible variations of the phase background that might result from the planned movements of the medical device(s) and/or the predicted or anticipated movements of the patient's body.

According to one embodiment of the present invention, medical device(s) may be set up in exactly or approximately the same configurations or arrangements as they would be during a subsequent, actual treatment procedure. For example, one or more medical devices may be placed at or near the locations where they should be during an upcoming treatment procedure. According to some embodiments, a medical device need not be positioned exactly as it would be during the planned treatment, i.e., the position of the device when a phase image is obtained need not correspond exactly to the position of the device when a reference image was obtained. An approximate match to a reference image is satisfactory (i.e., the reference image may be used as a baseline) as long as the difference is not clinically significant—i.e., sufficiently small (e.g., on the order of 1-2 degrees Celsius) as to be functionally equivalent for treatment purposes (within a margin of error that use of the closest reference image will not produce an adverse physiological effect).

This means that, instead of precise replication of the expected device positions and/or orientations during the "dry run," approximate positions will suffice as long as the resulting phase background does not differ, in a clinically significant manner, from what would result from an identical replication. Then, for each of those configurations or arrangements, a reference phase image may be acquired by scanning the MR imaging area.

According to another embodiment of the present invention, the patient may be instructed to lie still and breathe naturally as he or she is expected to behave during the actual treatment procedure. Then, at chosen moments during the patient's regular respiratory cycle (e.g., one or more moments during the inspiration phase and one or more moments during the expiration phase), reference phase images may be acquired to capture the movement or deformation of a region of interest in the image as well as any resulting change in the phase background. Similarly, the patient may be instructed to slightly move certain parts of his or her body (e.g., turning the head or sliding a hand), and a reference phase image may be acquired upon each of those movements or a combination thereof.

According to further embodiments of the present invention, the movements of the patient's body may be combined with the simulated setup of the medical device(s) such that more realistic reference phase images can be acquired. For example, a medical device may be moved to a new position and dwell at that position for a few minutes before being moved to another position. During those few minutes, the patient must still be breathing, and it is the breathing motion together with the new position of the medical device that alters the phase background. Therefore, it may be beneficial to capture multiple reference phase images corresponding to different stages of the patient's respiratory cycle while the medical device is in this new position. For ease of explanation, a scenario in which a reference phase image is acquired (i.e., an arrangement or configuration of the patient and the medical device(s) which resulted from movement(s) of either or both) is referred to hereinafter as "a patient-device scenario."

As a result, a number of reference phase images have been acquired in step 306, unlike prior PRF-based methods where only one reference phase image would be acquired. According to embodiments of the present invention, it is preferable that these reference phase images be acquired while the patient and/or the MR imaging area are maintained at a relatively stable pre-treatment temperature. The multiple reference phase images may be stored in a reference library or database, wherein each reference phase image may be tagged, annotated, or otherwise associated with its corresponding patient-device scenario. According to one embodiment of the present invention, the reference phase images may be computationally processed to facilitate query and/or comparison with other phase images.

In step 308, a first phase image is acquired by scanning the MR imaging area. The first phase image essentially captures the distribution of proton-resonance frequencies in the MR imaging area at the time of the acquisition step 308. Phase shifts reflected in the first phase image may include those that have been caused by non-temperature-related factors such as patient motion and/or movements of medical device(s).

Then, in step 310, one reference phase image is selected from the library of reference phase images which were acquired in step 306. Assuming the library of reference phase images covers all possible patient-device scenarios, one of those reference images has to be associated with or match the patient-device scenario in the first phase image. According to embodiments of the present invention, a number of methods may be employed to select the reference phase image that matches the patient-device scenario in the first phase image. For example, the library of reference phase images may be searched, for example, by examining the metadata of the images, to locate the reference image associated with a device setup that is the same as or closest to the device setup at the time of the acquisition step 308. Alternatively, the reference phase images themselves may be searched (or compared with the first phase image) to identify an image having physical features (e.g., position and shape of a tissue area) that closely match those in the first phase image.

The reference phase image so selected is used as a baseline reference for the first phase image in step 312. Since the selected reference phase image closely matches the patient-device scenario reflected in the first phase image, phase shifts may be calculated by subtracting the selected reference phase image from the first phase image as if no movement of the patient or the medical device(s) ever occurred between the acquisitions of those two images. Temperature changes may then be calculated based on the phase shifts. As a result, the use of the selected reference phase image as a baseline effectively reduces or eliminates measurement artifacts that arise from movements of objects in or near the MR imaging area.

According to some embodiments of the present invention, steps 308, 310, and 312 may be repeated as part of an MR thermal imaging process. For example, in an MRgFUS treatment procedure, steps 308, 310, and 312 may be performed prior to and/or after each sonication step to monitor temperature changes in a targeted tissue area. Since the patient's body and/or the MRgFUS treatment device(s) may have moved during the procedure, each iteration of steps 308, 310, and 312 may see a different reference phase image being selected and used as a baseline for temperature measurement.

Figure 4:
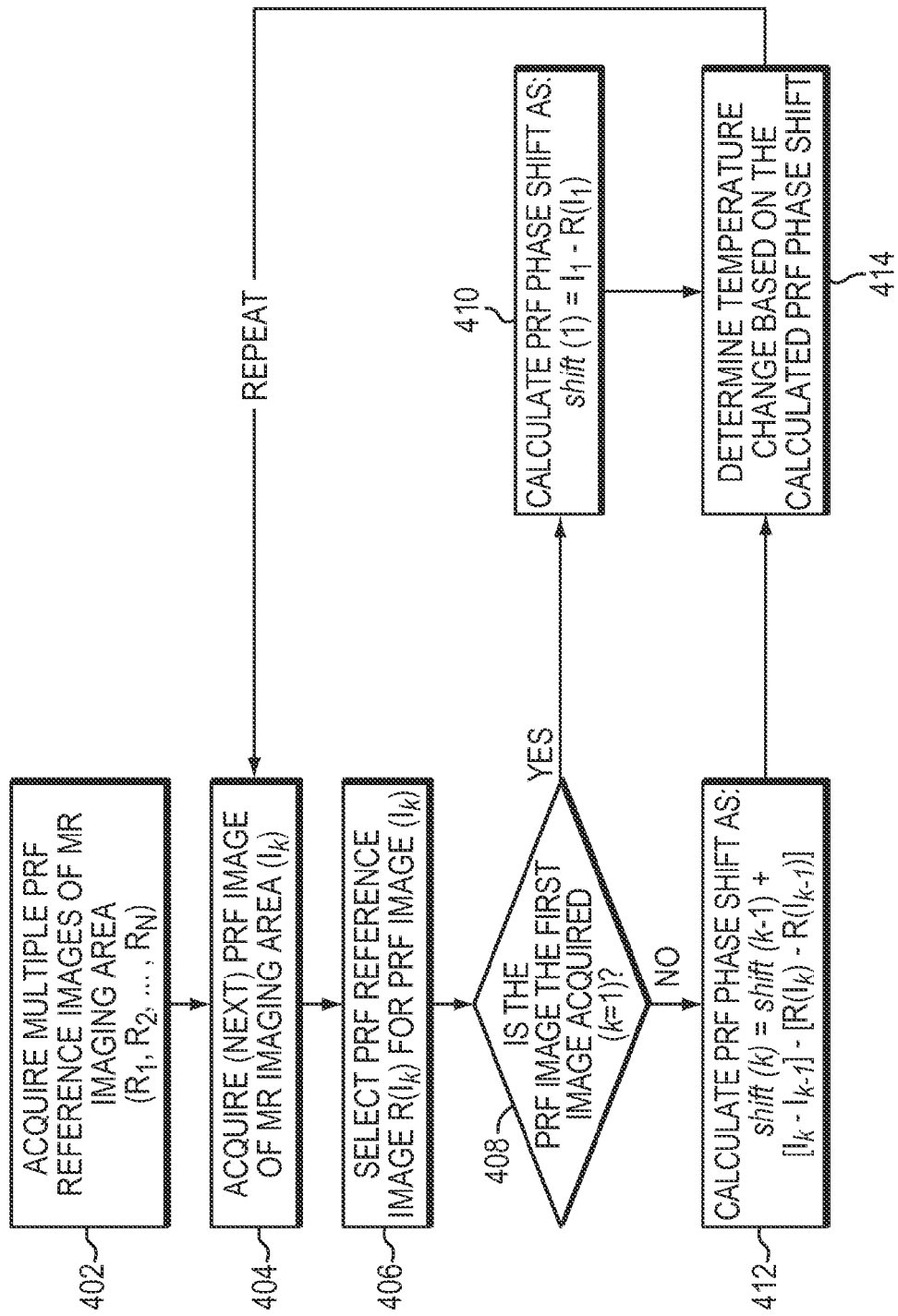
FIG. 4 shows a flow chart illustrating an exemplary method for correcting measurement artifacts in MR thermometry in accordance with another embodiment of the present invention.

FIG. 4 shows a flow chart illustrating an exemplary method for correcting measurement artifacts in MR thermometry in accordance with another embodiment of the present invention. In step 402, after a patient and/or medical device(s) are positioned in an MR unit, multiple reference phase images $(R_1, R_2, \ldots R_N)$ are acquired by scanning an MR imaging area. The multiple reference phase images $(R_1, R_2, \ldots R_N)$ may be candidate baseline images that correspond to different patient-device scenarios.

In step 404, a phase image $(I_k)$ is acquired by scanning the MR imaging area, wherein k is an integer that denotes the k-th acquisition of a phase image in a continuous series. The phase image $(I_k)$ captures a distribution of proton-resonance frequencies in the MR imaging area at the time of the acquisition step 404.

Then, in step 406, a reference phase image is selected from the library of multiple reference phase images $(R_1, R_2, \ldots R_N)$ based upon the phase image $(I_k)$ and/or the patient-device scenario at the time of the acquisition step 404. As mentioned earlier, the reference phase image may be selected by matching its physical features to those of the phase image $(I_k)$ and/or by matching a patient-device scenario associated with the reference phase image with the one associated with the phase image $(I_k)$. The reference phase image so selected may be denoted $R(I_k)$.

Next, in step 408, it is determined whether the phase image $(I_k)$ is the very first phase image acquired, that is, whether k equals one. If so, then, in step 410, the phase shift associated with the phase image (i.e., $I_1$) is calculated by subtracting the corresponding reference phase image $R(I_1)$ from the phase image $(I_1)$—

$$\text{shift}(1) = (I_1) - R(I_1).$$

If the phase image $(I_k)$ is not the first phase image acquired, then, in step 412, the phase shift associated with the phase image $(I_k)$ is calculated based on:
(i) the phase shift associated with the previous phase image $(I_{k-1})$, denoted shift(k−1); and
(ii) an incremental phase shift of the phase image $(I_k)$ as compared to the previous phase image $(I_{k-1})$, which is $[I_k - R(I_k)] - [I_{k-1} - R(I_{k-1})]$ or $[I_k - I_{k-1}] - [R(I_k) - R(I_{k-1})]$.

Thus, the phase shift associated with the phase image $(I_k)$ is $$\text{shift}(k) = \text{shift}(k-1) + [I_k - R(I_k)] - [I_{k-1} - R(I_{k-1})]$$
$$= \text{shift}(k-1) + [I_k - I_{k-1}] - [R(I_k) - R(I_{k-1})]$$

Steps 408, 410, and 412 together stand for the following mathematical proposition $$\text{shift}(k) = \left\{ \begin{array}{ll} I_1 - R(I_1) & \text{if } k = 1 \\ \text{shift}(k-1) + [I_k - I_{k-1}] - [R(I_k) - R(I_{k-1})] & \text{if } k > 1 \end{array} \right\}$$

The phase shift so calculated can then be used as the basis for determining temperature changes in step 414. Practically, each of the phase shift components shown above (i.e., shift (k), $[I_k - R(I_k)]$, and $[I_{k-1} - R(I_{k-1})]$) may be separately calculated as a scalar representing a pa thermal shift, and a final temperature change may be calculated by summing those partial thermal shifts. As mentioned above, the determination of each phase shift component may involve more than just a subtraction of scalars. Temperature changes relative to the reference temperature level(s) (at the time of the acquisition step 402) may be calculated pixel by pixel, thereby generating a thermal map of the MR imaging area. The process may loop back to step 404 where a next phase image is acquired by scanning the MR imaging area, and steps 404 through 414 may be repeated to generate the next thermal map.

As described above in connection with FIG. 4, the phase shift associated with each phase image is calculated incrementally, that is, by accumulating phase increments from all phase images heretofore acquired. Since each phase increment is calculated from consecutively scanned phase images, and due to selection of scanning parameters (e.g., TE and the time between consecutive scans), it is unlikely that the magnitude of any such phase increment will be large enough to exceed π. Therefore, unless a large change in temperature occurs rapidly between two consecutive scans, the measurement artifacts that arise from phase wrapping could be eliminated with the exemplar method illustrated in FIG. 4.

It should be noted that the exemplar method illustrated in FIG. 4 may be adapted for an MR thermal imaging process in which only a single reference image (instead of a library of references) is acquired and used as the baseline. The phase shift associated with each phase image may still be calculated incrementally, that is, based upon the phase shift associated with a previous phase image and the incremental phase change since the previous phase image.

Figure 5:
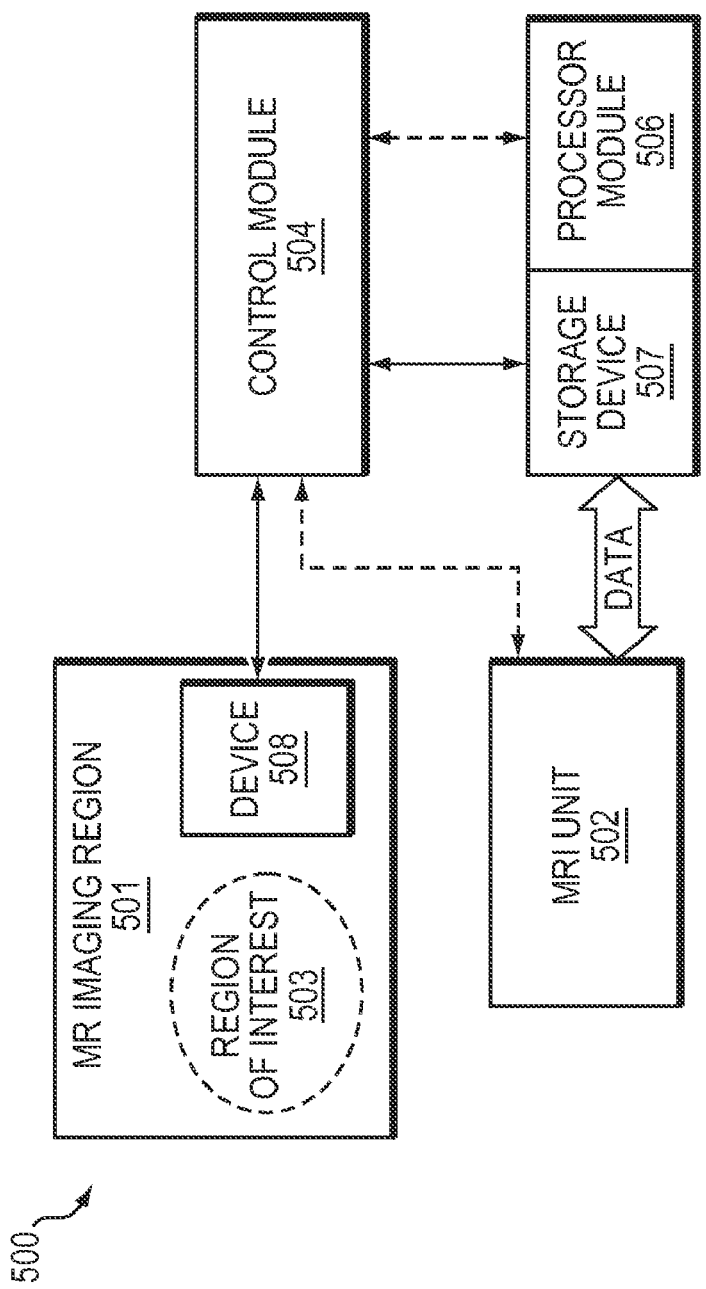
FIG. 5 shows a block diagram illustrating an exemplary system for correcting measurement artifacts in MR thermometry in accordance with an embodiment of the present invention.

FIG. 5 shows a block diagram illustrating an exemplary system 500 for correcting measurement artifacts in MR thermometry in accordance with an embodiment of the present invention. The system 500 comprises an MRI unit 502 having an imaging region 501. A patient's body or a portion thereof may be positioned in the imaging region 501 and a region of interest 503 may be identified. The MRI unit 502 may be configured for thermal imaging of the imaging region 501 and/or the region of interest 503 based on the PRF shift method. The system 500 may also comprise one or more medical devices 508 which are positioned in or near the MR imaging region 501 or the region of interest 503. A control module 504 in communication with the MRI unit 502 coordinates phase image acquisitions by the MRI unit 502. The control module 504 may further detect and/or control the placement of the medical device(s) 508. The image acquisition data from the MRI unit 502, as well as data indicating the patient-device scenarios, may be recorded in a storage device 507 and processed by a processor module 506 to implement the above-described techniques of correcting measurement artifacts in thermal imaging of the region of interest 503.

For example, according to one embodiment of the present invention, the control module 504 may cause the medical device(s) 508 to be positioned in or near the MR imaging region 501 according to a predetermined configuration for a treatment procedure. The control module 504 may also cause the MRI unit 502 to acquire a reference phase image of the MR imaging region 501 for each patient-device scenario, thereby accumulating a library of reference phase images. The library of reference phase images may be processed by the processor module 506 and stored in the storage device 507. Next, the control module 504 may cause the MRI unit 502 to acquire a first phase image of the MR imaging region. Then, based on the first phase image and/or a patient-device scenario concurrent with the first phase image, the processor module 506 may select a first reference phase image from the library of reference phase images. A first phase shift may be calculated either directly (by subtracting the first reference phase image from the first phase image) or incrementally according to the exemplary method illustrated in FIG. 4. Finally, the processor module 506 may calculate a distribution of temperature changes in the MR imaging region 501 or the region of interest 503 based on the first phase shift. The process may be repeated, for example, by acquiring a second phase image, selecting a second reference phase image, and then calculating a second phase shift, so on and so forth.

It should be noted that, although portions of the system 500 have been illustrated as discrete components in FIG. 5, some of these components (e.g., control module 504, processor module 506, and storage device 507) may be combined with one another and/or implemented as integral part(s) of the MRI unit 502. Other variations exist for configuring the system 500 as can be appreciated by those skilled in the art.

While the foregoing description includes many details and specificities, it is to be understood that these have been included for purposes of explanation only, and are not to be interpreted as limitations of the present invention. It will be apparent to those skilled in the art that other modifications to the embodiments described above can be made without departing from the spirit and scope of the invention. Accordingly, such modifications are considered within the scope of the invention as intended to be encompassed by the following claims and their legal equivalents.

What is claimed is:

1. A method of performing proton resonance frequency (PRF) based magnetic resonance (MR) temperature measurement, the method comprising the steps of:
   acquiring a plurality of PRF reference images of an MR imaging region, each of the reference images corresponding to a PRF phase background resulting from a different arrangement of one or more devices in or near the MR imaging region;
   acquiring a first PRF image of the MR imaging region subsequent to the acquisition of the plurality of PRF reference images;
   selecting, from the plurality of PRF reference images, a first PRF reference image most closely corresponding to the first PRF image;
   calculating a first PRF phase shift based at least in part on a difference between the first PRF image and the first PRF reference image;
   acquiring a second PRF image of the MR imaging region subsequent to the acquisition of the first PRF image;
   selecting, from the plurality of PRF reference images, a second PRF reference image most closely corresponding to the second PRF image;
   calculating a second PRF phase shift by summing (i) the first PRF phase shift and (ii) an incremental phase shift of a difference between the second PRF image and the second PRF reference image as compared to a difference between the first PRF image and the first PRF reference image; and
   determining at least one temperature change based on at least one of the first PRF phase shift and the second PRF phase shift.

2. The method of claim 1, wherein the plurality of PRF reference images correspond to predicted positionings of at least one treatment device.

3. The method of claim 2, wherein the treatment device comprises an MR guided focused ultrasound (MRgFUS) transducer.

4. The method of claim 1, further comprising:
   generating a temperature map of the MR imaging region based at least in part on the first PRF image and on the differences.

5. The method of claim 1, further comprising:
   calculating a movement compensation map based on differences between the first PRF reference image and the second PRF reference image.

6. The method of claim 1, further comprising:
   comparing the first PRF image with the plurality of PRF reference images to find matching physical features.

7. The method of claim 1, further comprising:
   acquiring a third PRF image of the MR imaging region subsequent to the acquisition of the second PRF image;
   selecting, from the plurality of PRF reference images, a third PRF reference image most closely corresponding to the second PRF image; and calculating a third PRF phase shift by summing (i) the second PRF phase shift and (ii) an incremental phase shift of a difference between the third PRF image and the third PRF reference image as compared to a difference between the second PRF image and the second PRF reference image.

8. A system for performing proton resonance frequency (PRF) based magnetic resonance (MR) temperature measurement, the system comprising:
an MRI unit;
a control module in communication with the MRI unit, and configured to cause the MRI unit to:
acquire a plurality of PRF reference images of an MR imaging region, each of the reference images corresponding to a PRF phase background resulting from a different arrangement of one or more devices in or near the MR imaging region,
acquire a first PRF image of the MR imaging region subsequent to the acquisition of the plurality of PRF reference images, and
acquire a second PRF image of the MR imaging region subsequent to the acquisition of the first PRF image; and
a processor module having access to image data acquired by the MRI unit, and configured to:
select, from the plurality of PRF reference images, a first PRF reference image most closely corresponding to the first PRF image,
calculate a first PRF phase shift based at least in part on a difference between the first PRF image and the first PRF reference image,
select, from the plurality of PRF reference images, a second PRF reference image most closely corresponding to the second PRF image,
calculate a second PRF phase shift by summing (i) the first PRF phase shift and (ii) an incremental phase shift of a difference between the second PRF image and the second PRF reference image as compared to a difference between the first PRF image and the first PRF reference image, and
determine at least one temperature change based on at least one of the first PRF phase shift and the second PRF phase shift.

9. A non-transitory computer-readable medium storing computer-executable codes for causing at least one processor to performing proton resonance frequency (PRF) based magnetic resonance (MR) temperature measurement, the computer-readable medium comprising:
computer-executable code for causing acquisition of a plurality of PRF reference images of an MR imaging region, each of the reference images corresponding to a PRF phase background resulting from a different arrangement of one or more devices in or near the MR imaging region;
computer-executable code for causing acquisition of a first PRF image of the MR imaging region subsequent to the acquisition of the plurality of PRF reference images;
computer-executable code for causing selection, from the plurality of PRF reference images, a first PRF reference image most closely corresponding to the first PRF image;
computer-executable code for causing calculation of a first PRF phase shift based at least in part on a difference between the first PRF image and the first PRF reference image;

computer-executable code for causing acquisition of a second PRF image of the MR imaging region subsequent to the acquisition of the first PRF image;
computer-executable code for causing selection, from the plurality of PRF reference images, a second PRF reference image most closely corresponding to the second PRF image;
computer-executable code for causing calculation of a second PRF phase shift by summing (i) the first PRF phase shift and (ii) an incremental phase shift of a difference between the second PRF image and the second PRF reference image as compared to a difference between the first PRF image and the first PRF reference image; and
computer-executable code for causing determination of at least one temperature change based on at least one of the first PRF phase shift and the second PRF phase shift.

10. A method of performing proton resonance frequency (PRF) based magnetic resonance (MR) temperature measurement, the method comprising the steps of:
acquiring a plurality of PRF reference images of an MR imaging region, each of the PRF reference images corresponding to a PRF phase background resulting from one or more predicted anatomical movements of at least a part of a patient's body;
acquiring a first PRF image of the MR imaging region subsequent to the acquisition of the plurality of PRF reference images;
selecting, from the plurality of PRF reference images, a first PRF reference image most closely corresponding to the first PRF image;
calculating a first PRF phase shift based at least in part on a difference between the first PRF image and the first PRF reference image;
acquiring a second PRF image of the MR imaging region subsequent to the acquisition of the first PRF image;
selecting, from the plurality of PRF reference images, a second PRF reference image most closely corresponding to the second PRF image;
calculating a second PRF phase shift by summing (i) the first PRF phase shift and (ii) an incremental phase shift of a difference between the second PRF image and the second PRF reference image as compared to corresponding pixels of a difference between the first PRF image and the first PRF reference image; and
determining at least one temperature change based on at least one of the first PRF phase shift and the second PRF phase shift.

11. The method of claim 10, further comprising:
predicting a trajectory for the one or more predicted anatomical movements.

12. The method of claim 11, wherein the predicted trajectory is associated with the patient's respiratory cycles.

13. The method of claim 10, further comprising:
acquiring a third PRF image of the MR imaging region subsequent to the acquisition of the second PRF image;
selecting, from the plurality of PRF reference images, a third PRF reference image most closely corresponding to the second PRF image; and
calculating a third PRF phase shift by summing (i) the second PRF phase shift and (ii) an incremental phase shift of a difference between the third PRF image and the third PRF reference image as compared to corresponding pixels of a difference between the second PRF image and the second PRF reference image.

14. A system for performing proton resonance frequency (PRF) based magnetic resonance (MR) temperature measurement, the system comprising:

an MRI unit;

a control module in communication with the MRI unit, and configured to cause the MRI unit to:

acquire a plurality of PRF reference images of an MR imaging region, each of the reference images corresponding to a PRF phase background resulting from one or more predicted anatomical movements of at least a part of a patient's body, acquire a first PRF image of the MR imaging region subsequent to the acquisition of the plurality of PRF reference images, and acquire a second PRF image of the MR imaging region subsequent to the acquisition of the first PRF image; and a processor module having access to image data acquired by the MRI unit, and configured to:

select, from the plurality of PRF reference images, a first PRF reference image most closely corresponding to the first PRF image, calculate a first PRF phase shift based at least in part on a difference between the first PRF image and the first PRF reference image, select, from the plurality of PRF reference images, a second PRF reference image most closely corresponding to the second PRF image, calculate a second PRF phase shift by summing (i) the first PRF phase shift and (ii) an incremental phase shift of a difference between the second PRF image and the second PRF reference image as compared to corresponding pixels of a difference between the first PRF image and the first PRF reference image, and determine at least one temperature change based on at least one of the first PRF phase shift and the second PRF phase shift.

15. A non-transitory computer-readable medium storing computer-executable codes for causing at least one processor to performing proton resonance frequency (PRF) based magnetic resonance (MR) temperature measurement, the computer-readable medium comprising:

computer-executable code for causing acquisition of a plurality of PRF reference images of an MR imaging region, each of the reference images corresponding to a PRF phase background resulting from one or more predicted anatomical movements of at least a part of a patient's body;

computer-executable code for causing acquisition of a first PRF image of the MR imaging region subsequent to the acquisition of the plurality of PRF reference images;

computer-executable code for causing selection, from the plurality of PRF reference images, a first PRF reference image most closely corresponding to the first PRF image;

computer-executable code for causing calculation of a first PRF phase shift based at least in part on a difference between the first PRF image and the first PRF reference image;

computer-executable code for causing acquisition of a second PRF image of the MR imaging region subsequent to the acquisition of the first PRF image;

computer-executable code for causing selection, from the plurality of PRF reference images, a second PRF reference image most closely corresponding to the second PRF image;

computer-executable code for causing a calculation of a second PRF phase shift by summing (i) the first PRF phase shift and (ii) an incremental phase shift of a difference between the second PRF image and the second PRF reference image as compared to corresponding pixels of a difference between the first PRF image and the first PRF reference image; and computer-executable code for causing determination of at least one temperature change based on at least one of the first PRF phase shift and the second PRF phase shift.

16. A method of performing proton resonance frequency (PRF) based magnetic resonance (MR) temperature measurement, the method comprising the steps of:

acquiring a plurality of PRF reference images of an MR imaging region associated with a patient, each of the reference images corresponding to a PRF phase background resulting from a different arrangement of one or more devices in or near the MR imaging region in combination with one or more predicted movements of the patient;

acquiring a first PRF image of the MR imaging region subsequent to the acquisition of the plurality of PRF reference images;

selecting, from the plurality of PRF reference images, a first PRF reference image most closely corresponding to the first PRF image;

calculating a first PRF phase shift based at least in part on a difference between the first PRF image and the first PRF reference image;

acquiring a second PRF image of the MR imaging region subsequent to the acquisition of the first PRF image;

selecting, from the plurality of PRF reference images, a second PRF reference image most closely corresponding to the second PRF image;

calculating a second PRF phase shift by summing (i) the first PRF phase shift and (ii) an incremental phase shift of a difference between the second PRF image and the second PRF reference image as compared to corresponding pixels of a difference between the first PRF image and the first PRF reference image; and determining at least one temperature change based at least in part on at least one of the first PRF phase shift and the second PRF phase shift.

* * * * *